United States Patent [19]

Baker

[11] 4,045,208

[45] Aug. 30, 1977

[54] DIPHENYL ETHER AMIDES

[75] Inventor: Don R. Baker, Orinda, Calif.

[73] Assignee: Stauffer Chemical Company, Westport, Conn.

[21] Appl. No.: 695,672

[22] Filed: June 14, 1976

Related U.S. Application Data

[62] Division of Ser. No. 598,486, July 23, 1975, Pat. No. 3,976,470.

[51] Int. Cl.² .................. A01N 9/22; C07D 207/04
[52] U.S. Cl. ................................. 71/95; 260/326.5 C
[58] Field of Search .................. 71/95; 260/326.5 C

[56] References Cited

U.S. PATENT DOCUMENTS

| | | | |
|---|---|---|---|
| 2,928,846 | 3/1960 | Bavley et al. | 260/326.5 C |
| 3,538,114 | 11/1970 | Himmele et al. | 71/95 X |
| 3,976,470 | 8/1976 | Baker | 260/455 A |

Primary Examiner—Joseph Paul Brust
Attorney, Agent, or Firm—Joel G. Ackerman

[57] ABSTRACT

Diphenyl ether amides having the formula

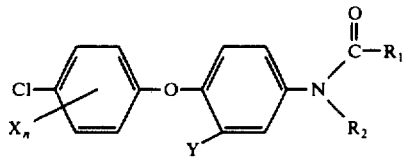

in which X is chloro or methyl; $n$ is zero, one or two; Y is chloro- or trifluoromethyl; $R_1$ is hydrogen, alkyl, lower alkoxy, lower haloalkyl, thio-lower alkyl, or alkenyl; $R_2$ is hydrogen, lower alkoxy-alkyl or lower alkanoyl; or $R_1$ and $R_2$ taken together is

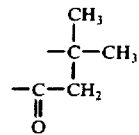

The compounds are useful as post-emergence herbicides, particularly as post-emergence, post-flooding herbicides, for use in connection with rice cultivation.

15 Claims, No Drawings

DIPHENYL ETHER AMIDES

This is a division of application Ser. No. 598,486, filed July 23, 1975, now U.S. Pat. No. 3,976,470, issued Aug. 24, 1976.

PRIOR ART

Certain diphenyl ether ureas are known to be useful as herbicides. For example, U.S. Pat. No. 3,119,682, discloses certain mono- and dialkylamino diphenyl ether ureas as suitable herbicides.

SUMMARY OF THE INVENTION

This application relates to novel diphenyl ether amides. In particular, this application relates to novel diphenyl ether amides having the formula

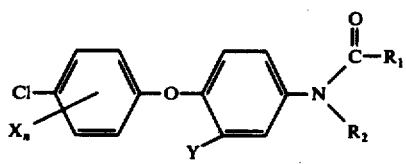

in which X is chloro or methyl; n is zero, one or two; Y is chloro or trifluoromethyl; $R_1$ is hydrogen, alkyl, lower alkoxy, lower haloalkyl, thio-lower alkyl, or alkenyl; $R_2$ is hydrogen, lower alkoxy-alkyl or lower alkanoyl; or $R_1$ and $R_2$ taken together is

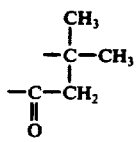

By the term "alkyl" is meant aliphatic radicals, both straight chain and branched chain, generally those having from 1 to about 10 carbon atoms, preferably from 1 to about 6 carbon atoms, for example, methyl, ethyl, n-propyl, iso-propyl, n-butyl, iso-butyl, t-butyl, n-amyl, iso-amyl, n-hexyl, heptyl, octyl, nonyl, decyl, etc. By the terms "lower alkoxy", "thio-lower alkyl", "lower haloalkyl", "lower alkoxy-alkyl", and "lower alkanoyl" are meant such groups containing from 1 to about 4 carbon atoms, for example, methoxy, ethoxy, propoxy, butoxy, thio-methyl, thio-ethyl, chloromethyl, dichloromethyl, trichloromethyl, trifluoromethyl, methoxymethyl, ethoxyethyl, ethoxymethyl, formyl, acetyl, propionyl, butyryl, isobutyryl, and the like. By the term "alkenyl" is meant an olefinic group having at least one olefinic bond and having from 2 to about 5 carbon atoms, for example, vinyl, allyl, propenyl, butenyl and the like.

The compounds of this invention have been found to be active herbicides, that is, certain members of the class have been found to be herbicidally effective against a wide range of plant species. More particularly, the compounds of the present invention are characterized by having little or no pre-emergence herbicidal activity, but having primarily post-emergence herbicidal activity, primarily affecting broad-leaf vegetation. The present compounds have been found to have particular utility in rice cultivation in selectively affecting the growth of weeds or other undesirable vegetation while leaving rice plants substantially unaffected. This invention also relates to a method of controlling undesirable vegetation comprising applying an herbicidally effective amount of a compound as above described to the area or plant locus where control is desired.

An herbicide as used herein, means a compound which controls or modifies the growth of plants. By the term "herbicidally effective amount" is meant an amount of compound which causes a modifying effect upon the growth of plants. By "plants" is meant germinant seeds, emerging seedlings and established vegetation, including the roots and above-ground portions. Such modifying effects include all deviations from natural development, for example, killing, retardation, defoliation, desiccation, regulation, stunting, tillering, stimulation, leaf burn, dwarfing, and the like.

In general, the compounds of the present invention are prepared by reacting a phenoxy aniline having the formula

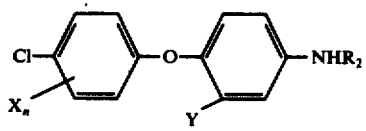

with an acyl chloride, alkyl chloroformate (when $R_1$ is lower alkoxy) or alkyl chlorothiolformate (when $R_1$ is thio-lower alkyl) having the formula

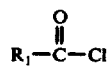

to produce the desired compound. X, $R_1$, $R_2$ and n are as defined above. The reaction is conducted in the presence of a hydrogen chloride acceptor such as a trialkyl amine or pyridine, or in the presence of sodium hydride, thus also producing, respectively, an amine hydrochloride or sodium chloride plus hydrogen. The 2,2-dimethylsuccinimides (compounds in which $R_1$ and $R_2$ taken together is

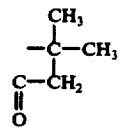

are prepared by reacting a phenoxy aniline having the formula

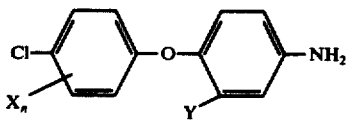

with 2,2-dimethylsuccinic acid in an acid medium, generally at a temperature of about 140° C or higher. The following are illustrative examples of preparation of representative compounds of the invention.

EXAMPLE 1

3-chloro-4-(4'-chlorophenoxy) propionanilide
(Compound 1 hereinbelow)

5.1 g (0.020 mole) 3-chloro-4-(4'-chlorophenoxy) aniline were mixed with 3.0 ml pyridine, 50 ml chloroform, and 2.1 ml (0.025 mole) propionyl chloride. The addition of the propionyl chloride caused the temperature of the mixture to rise from room temperature to 45° C. The mixture was allowed to stand overnight, then washed with 100 ml water, 50 ml of 1N hydrochloric acid and 50 ml of saturated sodium bicarbonate. It was then dried over sodium sulfate and evaporated in vacuo to give an oil which was crystallized from ether to give 4.5 g of a solid, m.p. 125°–127° C.

EXAMPLE 2

3-chloro-4(3',4'-dichlorophenoxy) propionanilide (Compound 5 hereinbelow)

37.4 g (0.13 mole) 3-chloro-4-(3',4'-dichlorophenoxy) aniline were mixed with 21 ml (0.13 mole) triethylamine and 150 ml methylene chloride. To the mixture were added 13.0 g (12.2 ml, 0.14 mole) propionyl chloride. The reaction became exothermic and an ice bath was used to stabilize temperature at about 25°–30° C. After all the components were added, the mixture was stirred for 1 hour and 20 minutes, washed with 150 ml water, 100 ml of 1N hydrochloric acid, and 100 ml of saturated sodium bicarbonate solution and dried over magnesium sulfate. The dried product was filtered, and solvents were stripped off. Amber crystals were obtained which were washed with n-pentane, vacuum filtered and dried in a vacuum oven at 80° C. There were obtained 42.65 g of crystals, m.p. 116°–118° C.

EXAMPLE 3

S-methyl-N-[3-chloro-4-(3',4'-dichlorophenoxy)-phenyl]-thiolcarbamate (Compound 7 hereinbelow)

The following were mixed together in a flask equipped with an electric stirrer: 37.4 g (0.13 mole) 3-chloro-4(3',4'-dichlorophenoxy)-aniline, 21 ml (0.15 mole) triethylamine, and 150 ml acetone. To the mixture were added dropwise 12.1 ml (0.14 mole) methyl chlorothiolformate. An ice bath was utilized to maintain the temperature at between 25° and 30° C. The mixture was stirred for 3 hours with addition of 200 ml chloroform. The product was washed with 150 ml water, 100 ml of 1N hydrochloric acid and 100 ml saturated sodium bicarbonate solution and dried with magnesium sulfate. The solvents were removed by rotary evaporation. A thick oil was formed which was re-crystallized from heptane, vacuum filtered and washed with n-pentane and dried at 80° C. in a vacuum oven. There were obtained 41.8 g of a solid, m.p. 103°–120° C.

EXAMPLE 4

N[4-(3',4'-dichlorophenoxy)-3-chlorophenyl]-propionimide (Compound 39 hereinbelow)

6.9 g of Compound 5, prepared in accordance with Example 2 above, (0.02 mole) were mixed with 50 ml dry tetrahydrofuran. There was added 0.58 g sodium hydride. The system was maintained under argon during this time, with electric stirring. After effervescence ceased, 1.7 ml (0.02 mole) propionyl chloride was added and the mixture stirred for 1½ hours. 200 ml of chloroform were then added, the mixture washed with water, dried over magnesium sulfate and solvents were removed by rotary stripping. There were obtained 7.9 g of an oil, $n_D^{30}$ – 1.5732.

The following Table I lists compounds representative of the invention.

TABLE I

| Compound Number | X | Y | $R_1$ | $R_2$ | m.p. or $N_D^{30}$ |
|---|---|---|---|---|---|
| 1 | — | Cl | $C_2H_5$ | H | 125–127° C |
| 2 | — | Cl | $SCH_3$ | H | 133–135° C |
| 3 | — | Cl | $CCl_3$ | H | 82–83° C |
| 4 | 3,5-$CH_3$ | Cl | $OCH_3$ | H | 67–69° C |
| 5 | 3-Cl | Cl | $C_2H_5$ | H | 110–112° C |
| 6 | 3-Cl | Cl | $OCH_3$ | H | Thick oil |
| 7 | 3-Cl | Cl | $SCH_3$ | H | Thick oil |
| 8 | 3-Cl | Cl | $CH_3$<br>$-\overset{\|}{C}-C_3H_7$<br>$\overset{\|}{CH_3}$ | H | 129–131° C |
| 9 | 3-Cl | Cl | $CH_3$<br>$-CH-C_3H_7$ | H | 68–70° C |
| 10 | 3-Cl | $CF_3$ | $SCH_3$ | H | $N_D^{30}$-1.5590 |
| 11 | 3-Cl | $CF_3$ | $C_2H_5$ | H | 110–112° C |
| 12 | 3-Cl | $CF_3$ | $OCH_3$ | H | Low melting solid |
| 13 | 3-Cl | $CF_3$ | $CH_3$<br>$-\overset{\|}{C}-C_3H_7$<br>$\overset{\|}{CH_3}$ | H | 102–104° C |
| 14 | 3-Cl | $CF_3$ | $CH_3$<br>$-CH-C_3H_7$ | H | 88–90° C |
| 15 | 3-$CH_3$ | Cl | $SCH_3$ | H | 114–118° C |
| 16 | 2-$CH_3$ | Cl | $SCH_3$ | H | Sticky solid |
| 17 | 3-$CH_3$ | Cl | $OCH_3$ | H | Sticky solid |
| 18 | 2-$CH_3$ | Cl | $C_2H_5$ | H | 117–119° C |
| 19 | 3-$CH_3$ | Cl | $C_2H_5$ | H | 115–117° C |
| 20 | 2-$CH_3$ | Cl | $CH_3$<br>$-\overset{\|}{C}-C_3H_7$<br>$\overset{\|}{CH_3}$ | H | 101–103° C |
| 21 | 3-$CH_3$ | Cl | $CH_3$<br>$-CH-C_3H_7$ | H | 65–67° C |
| 22 | 2-$CH_3$ | Cl | $CH_3$<br>$-CH-C_3H_7$ | H | 68–70° C |

TABLE I-continued

| Compound Number | X | Y | $R_1$ | $R_2$ | m.p. or $N_D^{30}$ |
|---|---|---|---|---|---|
| 23 | 3-$CH_3$ | Cl | $-\underset{\underset{CH_3}{\|}}{\overset{\overset{CH_3}{\|}}{C}}-C_3H_7$ | H | 114–118° C |
| 24 | 2-$CH_3$ | Cl | $OCH_3$ | H | Sticky semi-solid |
| 25 | 2-$CH_3$ | Cl | $SC_2H_5$ | H | 103–106° C |
| 26 | 3-$CH_3$ | Cl | $SC_2H_5$ | H | 115–120° C |
| 27 | 2-$CH_3$ | Cl | $CH_3\underset{\|}{C}=CH_2$ | H | Sticky semi-solid |
| 28 | 3-Cl | Cl | $SC_2H_5$ | H | 104–105° C |
| 29 | 3-Cl | Cl | $t\text{-}C_4H_9$ | H | 160–165° C |
| 30 | 3-Cl | Cl | $CH_3$ | H | 111–116° C |
| 31 | 3-Cl | Cl | $CH_3\underset{\|}{C}=CH_2$ | H | 85–94° C |
| 32 | 3-Cl | Cl | $-CH=CH_2$ | H | 68–82° C |
| 33 | 3-Cl | Cl | $-\underset{\underset{}{}}{\overset{\overset{CH_3}{\|}}{CH}}-C_3H_7$ | H | 87–90° C |
| 34 | 3-Cl | Cl | $C_2H_5$ | $-CH_2-O-C_2H_5$ | $N_D^{30}$-1.5758 |
| 35 | 2-Cl | Cl | $-\underset{\underset{}{}}{\overset{\overset{CH_3}{\|}}{CH}}-C_3H_7$ | H | 108–110° C |
| 36 | 2-Cl | Cl | $C_2H_5$ | H | 125–127° C |
| 37 | 2-Cl | Cl | $SCH_3$ | H | 120–121° C |
| 38 | 2-Cl | Cl | $OCH_3$ | H | Thick oil |
| 39 | 3-Cl | Cl | $C_2H_5$ | $-\overset{\overset{O}{\|\|}}{C}-C_2H_5$ | $N_D^{30}$-1.5732 |
| 40 | 2-Cl | Cl | $C_2H_5$ | $-\overset{\overset{O}{\|\|}}{C}-C_2H_5$ | $N_D^{30}$-1.5871 |
| 41 | 2-Cl | Cl | $-\underset{\underset{}{}}{\overset{\overset{CH_3}{\|}}{CH}}-C_3H_7$ | $-\overset{\overset{O}{\|\|}}{C}-C_2H_5$ | $N_D^{30}$-1.5457 |
| 42 | 2-Cl | Cl | $SCH_3$ | $-\overset{\overset{O}{\|\|}}{C}-C_2H_5$ | Thick oil |
| 43 | 3-Cl | Cl | $SCH_3$ | $-\overset{\overset{O}{\|\|}}{C}-C_2H_5$ | 75° C |
| 44 | 3-Cl | Cl | $-\underset{\underset{\overset{\|\|}{O}}{\overset{\|}{C}}=CH_2}{\overset{\overset{CH_3}{\|}}{C}-CH_3}$ | | 111–114° C |
| 45 | 3-Cl | Cl | H | H | 134° C |
| 46 | 3-Cl | Cl | $SCH_3$ | $-CH_2-O-C_2H_5$ | $N_D^{30}$-1.5985 |
| 47 | 2-Cl | Cl | $-\underset{\underset{\overset{\|\|}{O}}{\overset{\|}{C}}=CH_2}{\overset{\overset{CH_3}{\|}}{C}-CH_3}$ | | 120° C |

HERBICIDAL SCREENING TESTS

The representative compounds in the foregoing Table I were tested as herbicides in the following manner:

A. Pre-emergence Herbicide Screening Test: Using an analytical balance, 20 mg of the compound to be tested is weighed out on a piece of glassine weighing paper. The paper and compound are placed in a 30-ml wide-mouth bottle and 3 ml of acetone containing 1% Tween 20 is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small Styrofoam flat one day after planting weed seeds in the flat or soil. A No. 152 DeVilbiss atomizer is used to apply the spray using compressed air at a pressure of 5 lb/sq. inch.

On the day preceding treatment, the Styrofoam flat, which is 7 inches long, 5 inches wide and 2.75 inches deep is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica juncea*) and curly dock (*Rumex crispus*). Ample seeds are planted to give about 20 to 50 seedlings per row after emergence, depending on the size of the plants.

After treatment, the flats are placed in the greenhouse at a temperature of 70° to 85° F and watered by sprinkling. Two weeks after treatment, the degree of injury or control is determined by comparison with untreated check plants of the same age. The injury rating from 0 to 100% is recorded for each species as percent control with 0% representing no injury and 100% representing complete kill.

B. Post-emergence Herbicide Screening Test: Seeds of six plant species, including hairy crabgrass, watergrass, red oat, mustard, curly dock and pinto beans (*Phaseolus vulgaris*) are planted in the Styrofoam flats as described above for pre-emergence screening. The flats are placed in the greenhouse at 70° to 85° F and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20 and then adding 5 ml of water. The solution is sprayed on the foliage using a No. 152 DeVilbiss atomizer at an air pressure of 5 lb/sq. inch.

The results of these tests are shown in Table II. Compounds 1-4 were tested at 20 lbs/acre; the remaining compounds were tested at 8 lbs/acre. The values given for Compounds 1-4 relate to percent control for seven plant species tested pre-emergence and six plant species tested post-emergence; with respect to pre-emergence, a value of 21 indicates 70 to 100% control; with respect to post-emergence, a value of 18 indicates 70 to 100% control. The values given for Compounds 5-47 indicate an average of control for seven plant species in pre-emergence tests and six plant species in post-emergence tests, with respect to 100% control.

C. Post-flood - Post-emergence Application to Paddy Rice:

Plastic tubs, 10 ×7.5 × 5.75 inches were filled to a depth of 2 inches with 8 pounds of a loamy sand soil pretreated with 50 ppm Captan 50W and 18. 18. 18 fertilizer. One pint of the soil was removed, the remaining soil was leveled and seven rows were impressed across the width of the flat. Three dayflower (*Commelina diffusa*) cuttings 3 to 4 inches long, six yellow nutsedge tubers (*Cyperus esculentus*), and seeds of annual morning-glory (*Ipomoea purpurea*), curly dock (*Rumex crispus*), sesbania (*Sesbania spp.*) and rice (*Oryza sativa*) were planted in separate rows. The pint of soil was used to cover 0.5 inches deep the seeds, tubers and part of the cuttings. The planted soil was placed in a greenhouse, and irrigated by sprinkling as needed to keep the soil moist. Three days after the initial seeding another row was impressed 0.5 inches deep across the width of the flat and seeds of watergrass (*Echinochloa crusgalli*) were planted and covered by pinching together the soil on either side of the seeder row. Seven to ten days after the original seeding, the soil was flooded with 2 inches of water. At flooding time the grass species were in the two leaf stage 1 to 2 inches high, the nutsedge was 1 inch high, the curly dock was in the cotyledon stage about 1 inch high, the other broadleaf species were 2 to 3 inches high and the day flower was rooted with little new growth. Test compounds were applied by pipetting into the flood water a stock solution of test compound dissolved in 20 ml of acetone containing 1% Tween 20 at a level proportionate to 2 lb/acre of the test compound. The water level in the tubs was maintained by adding water as needed. Three weeks after application the species were rated visually as percent control from 0 to 100%, where 0% represents no injury and 100% represents complete kill when compared to the untreated check. The rice was substantially unaffected. The percent control was based on the total injury to the other plants.

The results of this test are given in Table II under the heading "Post-flood - Rice" in terms of percent control of species other than rice, with respect to 100% control.

TABLE II

| Compound Number | Pre-Emergence Control | Post-Emergence Control | Post-flood- Rice |
|---|---|---|---|
| 1 | 6 | 14 | 63 |
| 2 | 3 | 15 | 67 |
| 3 | 2 | 12 | 32 |
| 4 | 7 | 15 | 43 |
| 5 | 30 | 72 | 67 |
| 6 | 0 | 71 | 67 |
| 7 | 11 | 72 | 75 |
| 8 | 0 | 50 | 67 |
| 9 | 37 | 73 | 67 |
| 10 | 0 | 78 | 65 |
| 11 | 41 | 90 | 63 |
| 12 | 19 | 60 | 63 |
| 13 | 0 | 0 | 28 |
| 14 | 6 | 64 | 58 |
| 15 | 0 | 53 | 67 |
| 16 | 0 | 63 | 47 |
| 17 | 1 | 44 | 23 |
| 18 | 37 | 52 | 60 |
| 19 | 7 | 68 | 60 |
| 20 | 9 | 30 | 50 |
| 21 | 0 | 62 | 70 |
| 22 | 0 | 58 | 60 |
| 23 | 0 | 17 | 46 |
| 24 | 0 | 37 | 56 |
| 25 | 0 | 25 | 54 |
| 26 | 0 | 0 | 40 |
| 27 | 0 | 51 | 58 |
| 28 | 0 | 52 | 67 |
| 29 | 0 | 66 | 67 |
| 30 | 0 | 72 | 67 |
| 31 | 0 | 95 | 80 |
| 32 | 0 | 75 | 67 |
| 33 | 10 | 88 | 80 |
| 34 | 0 | 80 | 67 |
| 35 | 13 | 73 | 88 |
| 36 | 29 | 70 | 86 |
| 37 | 0 | 90 | 80 |
| 38 | 0 | 84 | — |
| 39 | 6 | 99 | 57 |
| 40 | 0 | 96 | 100 |
| 41 | 4 | 99 | 100 |
| 42 | 0 | 80 | 69 |
| 43 | 0 | 77 | 74 |
| 44 | 0 | 18 | 62 |
| 45 | 0 | 30 | 72 |
| 46 | 0 | 50 | 67 |
| 47 | 0 | 27 | — |

In practice, the compounds are formulated with an inert carrier, utilizing methods well-known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.5 to approximately 50 pounds per acre.

The compositions of the present invention are most advantageously applied at the post-emergent, post-flood stage, for example by spraying from either aircraft or with hand-held or other ground level sprayers. Incorporation of the compounds into the flood water is most advantageously performed when the rice is at a height of several inches above the water; if applied too early the compounds could cause injury to very young rice plants, if applied much later the compounds would not be as effective against fully-grown weed species.

What is claimed is:

1. A compound having the formula

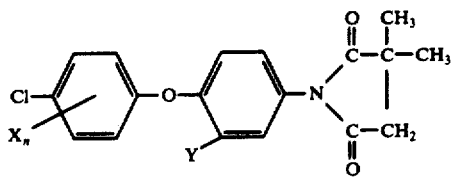

in which X is chloro or methyl; n is 0, 1 or 2; and Y is chloro or trifluoromethyl.

2. A compound according to claim 1 in which X is chloro.

3. A compound according to claim 2 in which X is 3-chloro.

4. A compound according to claim 2 in which X is 2-chloro.

5. A compound according to claim 1 in which Y is chloro.

6. A compound according to claim 1 in which Y is chloro and X is 3-chloro.

7. A compound according to claim 1 in which Y is chloro and X is 2-chloro.

8. A method of controlling undesirable vegetation comprising applying to the vegetation or the locus thereof subsequent to the emergence of such vegetation, an herbicidally effective amount of a compound having the formula

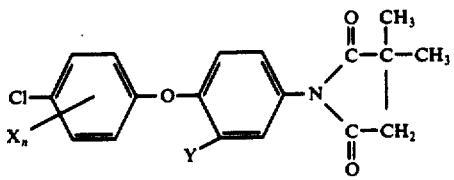

in which X is chloro or methyl; n is 0, 1 or 2; and Y is chloro or trifluoromethyl.

9. A method according to claim 8 in which X is chloro.

10. A method according to claim 9 in which X is 3-chloro.

11. A method according to claim 9 in which X is 2-chloro.

12. A method according to claim 8 in which Y is chloro.

13. A method according to claim 8 in which Y is chloro and X is 3-chloro.

14. A method according to claim 8 in which Y is chloro and X is 2-chloro.

15. An herbicidal composition of matter comprising:
   a. an herbicidally effective amount of a compound having the formula

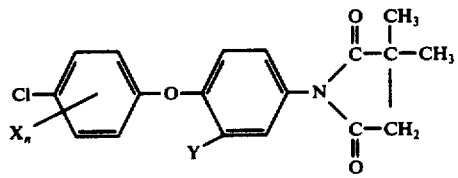

in which X is chloro or methyl; n is 0, 1 or 2; and Y is chloro or trifluoromethyl; and
   b. an inert carrier.

* * * * *